United States Patent [19]

Patoiseau et al.

[11] Patent Number: 5,025,015
[45] Date of Patent: Jun. 18, 1991

[54] THIOFORMAMIDINES, AND USE AS MEDICAMENTS

[75] Inventors: Jean F. Patoiseau, Castres; Jean-Marie Autin, Labruguiere; Henri Cousse, Castres; Véronique Sales, Dijon; Jacky Tisne-Versailles, Castres; Jean-Pierre Bali, Montpellier Cédex, all of France

[73] Assignee: Pierre Fabre Medicament, Paris, France

[21] Appl. No.: 404,337

[22] Filed: Sep. 7, 1989

[30] Foreign Application Priority Data

Sep. 8, 1988 [FR] France ................... 88 11747

[51] Int. Cl.$^5$ ............... A61K 31/505; A61K 31/415; A61K 31/41; C07D 239/38
[52] U.S. Cl. .................... 514/274; 514/385; 514/398; 514/256; 514/401; 514/395; 514/384; 514/359; 544/316; 548/337; 548/351; 548/329; 548/255; 548/264.4; 548/300
[58] Field of Search ............... 548/337, 351, 329, 255, 548/264.4, 300; 544/316; 514/274, 256, 384, 385, 401, 359, 398, 395

[56] References Cited

U.S. PATENT DOCUMENTS 4,735,955 4/1988 Tomiyama et al. ................ 514/374

Primary Examiner—John M. Ford
Attorney, Agent, or Firm—Gordon W. Hueschen

[57] ABSTRACT

Formamidine compounds of general formula I

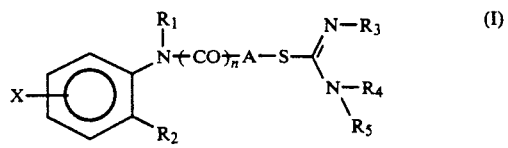

in which:

$R_1$ represents H or $C_{1-4}$ alkyl, $R_2$ represents benzoyl, benzyl, or alphahydroxybenzyl, the aromatic ring being optionally substituted by a halogen atom, $R_3$ and $R_4$, which are identical or different, represent hydrogen, lower-alkyl, or lower-alkenyl, or form between them with the formamidine function a heterocycle, $R_5$ represents hydrogen or $C_{1-4}$ lower-alkyl or forms with $R_4$ a double bond ($-N=R_4$) in the case of pseudoaromatic heterocycles, n equals 0 or 1, A represents a linear or branched $C_{1-4}$ alkylene chain, X represents hydrogen, halogen, $C_{1-4}$ lower-alkyl, $C_{1-4}$ lower-alkoxy, or nitro, and pharmaceutically-acceptable salts thereof, are disclosed.

The compounds and pharmaceutical compositions thereof are used, optionally in combination with other active principles, as drugs for the treatment of gastrointestinal ailments, especially as gastric antisecretory and antiulcer agents.

6 Claims, No Drawings

THIOFORMAMIDINES, AND USE AS MEDICAMENTS

BACKGROUND OF INVENTION AND PRIOR ART

1. Field of Invention

Gastric antisecretory and antiulcer compounds, compositions, and treatment; novel thioformamidines useful for such purpose.

2. Prior Art

Cimetidine [(N-Cyano-N'-methyl-N''-[2-[[(5-methyl-1H-imidazol-4-yl)methyl]thio]ethyl]guanidin e; Tagamet (TM)] is a renowned antagonist to histamine $H_2$ receptors, especially in the treatment of duodenal and gastric ulcers, and therefore is a compound which may advantageously be employed as a standard when testing the effectiveness of another compound against excessive gastric secretion and ensuing ulcers.

The compounds of the present invention, which are novel formamidines, are superior to cimetidine in their gastric antisecretory effect and approximately equal thereto in the inhibition of ulcer lesions.

OBJECTS OF THE INVENTION

An object of the invention is to provide novel formamidines which are effective gastric antisecretory agents, pharmaceutical compositions thereof, and a method of treating excessive gastric secretions and inhibiting ulcer formation therewith. Other objects of the invention will become apparent hereinafter, and still others will be obvious to one skilled in the art.

SUMMARY OF THE INVENTION

The present invention, inter alia, comprises novel formamidine compounds, pharmaceutical compositions thereof, a method of reducing excess gastric secretion and inhibiting the formation of ulcer lesions therewith, all as set forth in more detail hereinafter and as claimed in the claims appended hereto.

THE INVENTION

The present invention, developed at the Pierre Fabre Research Center, has as its object new chemical compounds, their method of preparation, pharmaceutical compositions thereof, and their use as drugs. The new chemical compounds are selected from those having the general Formula I:

[Formula I structure]

in which:

- $R_1$ represents hydrogen or lower-alkyl containing one to four carbon atoms, inclusive,
- $R_2$ is benzoyl, benzyl, or alpha-hydroxybenzyl, the aromatic ring being optionally substituted by a halogen atom,
- $R_3$ and $R_4$, which are identical or different, represent hydrogen, lower $C_{1-4}$ alkyl, or lower $C_{1-4}$ alkenyl, or, together with the formamidine function, form a heterocycle, such as, for instance, imidazole, imidazoline, benzimidazole, triazole, pyrimidine, or tetrahydropyrimidine,
- $R_5$ represents hydrogen, or lower-alkyl containing 1 to 4 carbon atoms, inclusive, or forms with $R_4$ a double bond ($-N=R_4$) in the case of pseudoaromatic heterocycles,
- n equals 0 or 1,
- A represents a linear or branched alkylene group having 1 to 4 carbon atoms, inclusive, and
- X represents hydrogen, halogen, lower $C_{1-4}$ alkyl, lower $C_{1-4}$ alkoxy, or nitro, and pharmaceutically-acceptable organic and inorganic salts thereof.

The present invention also concerns a method of preparing compounds of Formula I by reaction of a thioformamidine with a halogenated reagent:

[Formulas II and III]

wherein

Y represents chlorine or bromine, and $R_1$, $R_2$, $R_3$, $R_4$, $R_5$, A, n and X have the same meaning as given in the foregoing.

The reaction is preferably carried out in an organic solvent such as methanol or ethanol and under reflux.

The present invention moreover also concerns the use of compounds of Formula I as drugs as well as pharmaceutical compositions containing these compounds.

The pharmaceutical compositions of the present invention may contain one or more compounds of Formula I, possibly in association with other active principles. Among the compounds of Formula I, mention may be made more particularly of the following specific compounds, all of which are produced in accord with the following Examples:

N-methyl 2-[2-($\Delta$2-imidazolinyl)thio]2'-orthochlorobenzoyl-4'-chloroacetanilide hydrochloride. (1)

[Structure]

M = 458,79
F° = 202° C.

N-methyl 2-2-($\Delta$2-imidazolinyl)thio] 2'-benzoyl-4'-chloroacetanilide hydrochloride. (2)

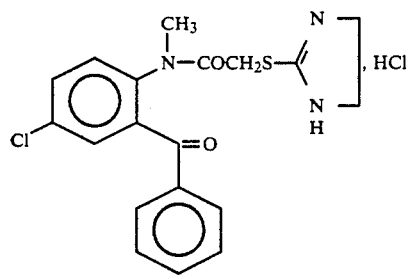

M = 424,35
F° = 202° C.

2-[2-(Δ2-imidazolinyl)thio] 2'-orthochlorobenzoyl-4'-chloroacetanilide hydrochloride. (3)

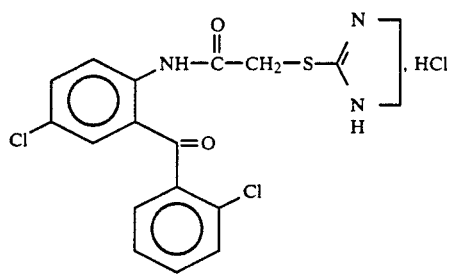

M = 444.76
F° = 184° C.

N-methyl 2-[2-(1-methylimidazolyl)thio] 2'-orthochlorobenzoyl-4'-chloroacetanilide hydrochloride. (4)

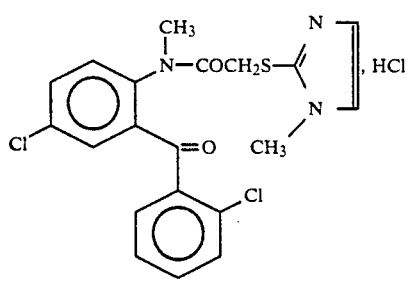

M = 470,8
F° = 186° C.

2-(2-imidazolylthio) 2'-benzoyl-4'-chloroacetanilide hydrochloride. (5)

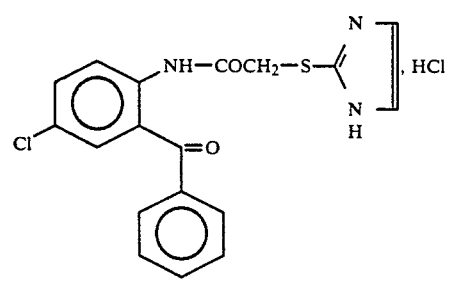

M = 408,31
F° = 194° C.

2-(2-imidazolylthio) 2'-orthochlorobenzoyl-4'-chloroacetanilide hydrochloride. (6)

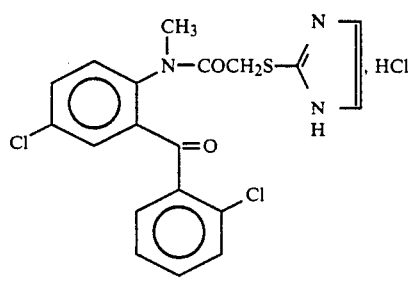

M = 442,75
F° = 178° C.

N-methyl 2-orthochlorobenzoyl-4'-chloro 2-[(2-imidazolyl)thio]acetanilide hydrochloride. (7)

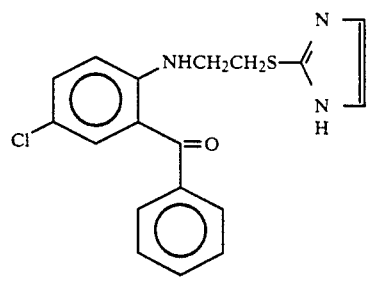

M = 456,78
F° = 165° C.

1-(2-imidazolylthio) 2-[(2-benzoyl-4-chloro)anilino]ethane. (8)

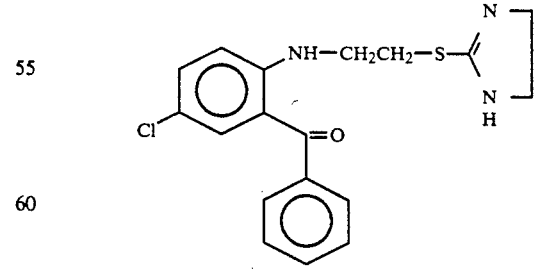

M = 357,86
F° = 203° C.

1-[2-(Δ2-imidazolinyl)thio] 2-(2-benzoyl-4-chloro)anilinoethane. (9)

M = 359,87
F° = 146° C.

N-methyl 2'-orthochlorobenzoyl-4'-chloro 2-[2-(1-methyl-Δ2-imidazolinyl)thio]acetanilide hydrochloride. (10)

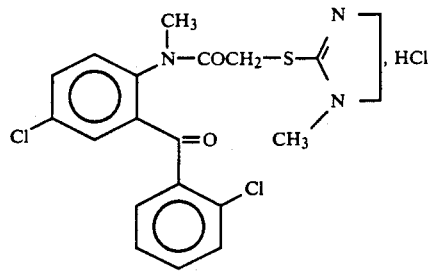

M = 472,83
F° = 185° C.

N-methyl 2'-(orthochloro-α-hydroxybenzyl)-4'-chloro 2-[2-(Δ2-imidazolinyl)thio]acetanilide. (11)

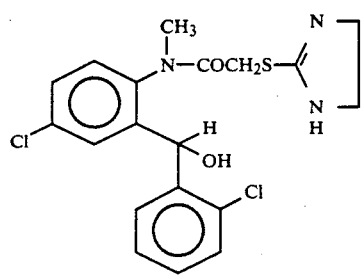

M = 424,35
F° = 170° C.

N-methyl 2'-benzyl-4'-chloro 2-[2-(Δ2-imidazolinyl)thio]acetanilide hydrochloride. (12)

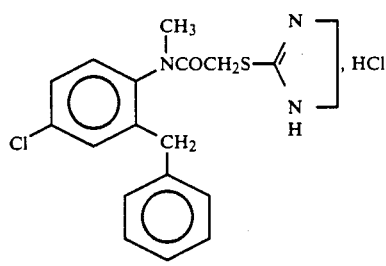

M = 410,35
F° = 217° C.

N-methyl 2'-orthochlorobenzoyl-4'-chloro 2-[2-(Δ2-imidazolinyl)thio]propionanilide citrate. (13)

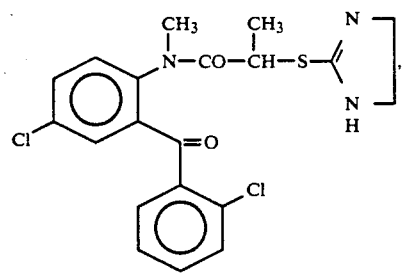

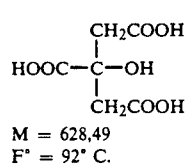

M = 628,49
F° = 92° C.

N-methyl 2'-benzoyl 2-[2-imidazolylthio]acetanilide. (14)

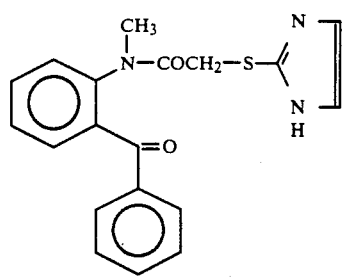

M = 351,43
F° = 107° C.

N-methyl 2'-benzoyl-4'-chloro 2-(2-imidazolylthio)acetanilide hydrochloride. (15)

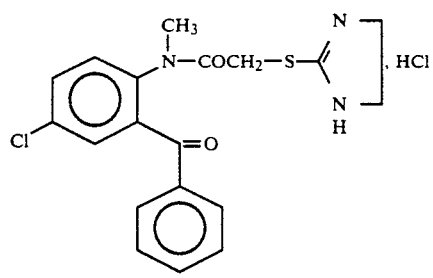

M = 422,33
F° = 180° C.

N-methyl 2'-orthochlorobenzoyl-4'-chloro 2-isothioureidoacetanilide hydrochloride. (16)

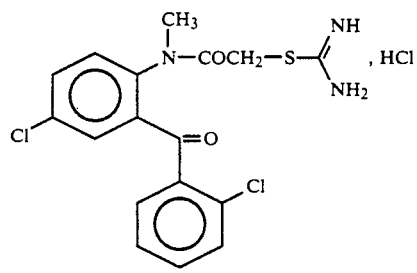

M = 432,76
F° = 195° C.

N-methyl 2'-orthochlorobenzoyl-4'-chloro 2-(2-pyrimidinyl)thioacetanilide. (17)

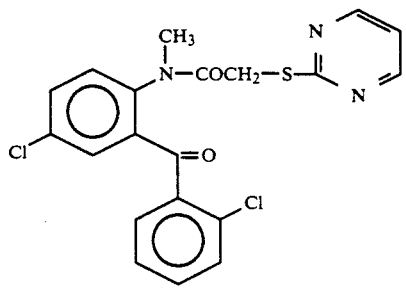

M = 432,33
F° = 138° C.

N-methyl 2'-orthochlorobenzoyl-4'-chloro 2-(1-ethyl-2-imidazolyl)thioacetanilide hydrochloride. (18)

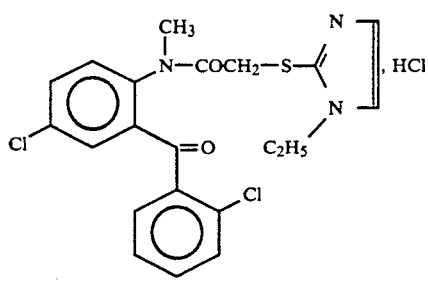

M = 484,83
F° = 172° C.

N-methyl 2'-orthochlorobenzoyl-4'-chloro 3-(2-imidazolyl)thiopropionanilide. (19)

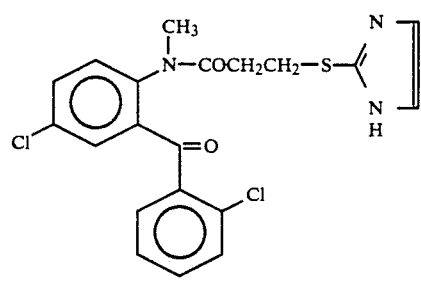

M = 434,34
F° = 95° C.

N-methyl 2'-benzoyl-4'-nitro 2-[(2-imidazolyl)thio]acetanilide hydrochloride. (20)

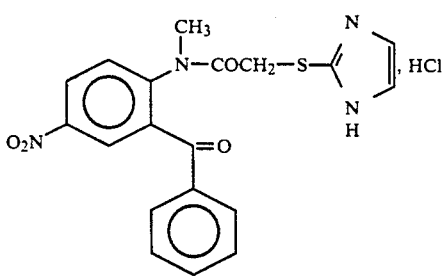

M = 432,88
F° = 205° C.

N-methyl 2'-orthofluorobenzoyl-4'-chloro 2-[(2-imidazolyl)thio]acetanilide hydrochloride. (21)

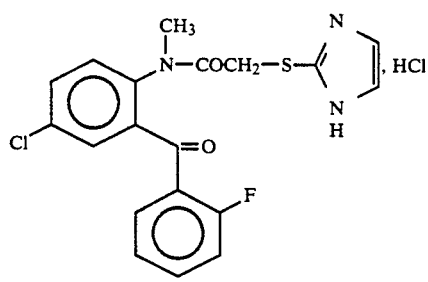

M = 440,12
F° = 166° C.

N-methyl 2'-benzoyl-4'-methoxy 2-[(2-imidazolyl)thio]acetanilide hydrobromide. (22)

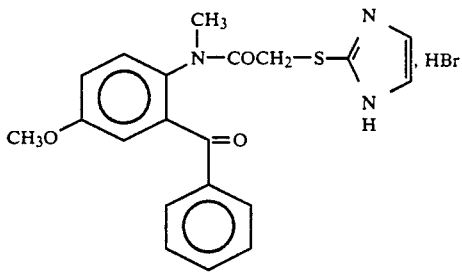

M = 462,37
F° = 128° C.

DETAILED DESCRIPTION OF THE INVENTION

The invention will now be described in further detail by the following non-limitative examples:

EXAMPLE 1

Preparation of N-methyl 2-[2-(Δ2-imidazolinyl)thio]2'-benzoyl-4'-chloroacetanilide hydrochloride. (2)

22.55 grams of N-methyl 2'-benzoyl-2,4'-dichloroacetanilide and 6.13 grams of ethylene thiourea are refluxed for 6 hours in 150 ml of absolute ethanol. The solution is evaporated under vacuum and taken up in a minimum amount of chloroform and then diluted with ethyl ether. Upon crystallization, 23.6 grams are obtained of N-methyl 2-[2-(Δ2-imidazolinyl)thio]2'-benzoyl-4'-chloroacetanilide hydrochloride (yield =92%).

MP=202° C.

C.C.M.=silica gel Merck 60 F 254; solvent: CHCl₃—MeOH :

85-15 - Rf=0.27.

EXAMPLE 2

N-methyl 2'-orthochlorobenzoyl-4'-chloro 2-[(2-imidazolyl)thio]acetanilide hydrochloride. (7)

A suspension of 10.68 grams of N-methyl 2'-orthochlorobenzoyl-2,4'-dichloroacetanilide and 2.4 grams of 2-mercaptoimidazole are treated for 8 hours under reflux with methanol. After cooling, evaporation under vacuum, and taking up by an acetone-ether mixture, there is obtained by crystallization the hydrochloride of N-methyl 2'-orthochlorobenzoyl-4'-chloro 2-[(2-imidazolyl)thioacetanilide (9.12 g).

MP=165° C.

Rf=0.22 (ethyl acetate)

EXAMPLE 3

1-[2-(Δ2-imidazolinyl)thio] 2-(2-benzoyl-4-chloro)anilinoethane. (9)

A suspension of 16.9 grams of β-bromo-2-ethylamino-5-chlorobenzophenone and 5 grams of ethylene thiourea is refluxed for 3 hours with a solution containing 100 ml of 95° ethanol, 10 ml of 10N sodium hydroxide and 15 ml of water. After evaporation in vacuum, taking up by absorption in 6N hydrochloric acid, and washing with ethyl acetate, the aqueous phase is neutralized with sodium bicarbonate and extracted with ethyl acetate. The concentrated organic phase is purified over a silica column by elution with MeOH—NHCl₃—NH₄OH / 9-90-1 and the 1-[2-(Δ2- imidazolinyl)thio]2-(2-benzoyl-4-chloro)anilinoethane is isolated by crystallization;
MP=146° C.
Rf=0.13 (CHCl$_3$—MeOH : 85-15)

EXAMPLE 4

N-methyl 2'-(orthochloro-alpha-hydroxybenzyl)-4'-chloro 2-[2-(Δ2-imidazolinyl)thio]acetanilide. (11)

750 mg of sodium borohydride are added in individual portions to a suspension of 2.8 grams of 2-methylamino-2',5-dichlorobenzophenone in 20 ml of methanol. After reaction for about ten minutes, the solvent is evaporated in a vacuum. After absorption in ether, washing with water, and then drying, 2-methylamino-2',5-dichlorobenzhydrol is isolated by crystallization (2.52 g).
MP=110° C.

The compound obtained (2.26 g) in solution in ethyl acetate is treated at a temperature of 0° C. with 0.8 ml of bromoacetyl chloride in solution in ethyl acetate (10 ml). After washing with water and drying, 2-(N-methylbromacetamido)-2',5-dichlorobenzhydrol is obtained (2.83 g). MP=196° C.

This product (6.5 g) in suspension in absolute ethanol (30 ml) is treated with ethylene thiourea (1.63 g) under reflux for three hours. After cooling, crystals are obtained which are filtered out and washed with ether. Upon absorption in 1N sodium hydroxide, extraction by THF-ethyl acetate and then drying and recrystallizing from ethyl acetate, N-methyl 2'-(orthochloro-alpha-hydroxybenzyl)-4'-chloro 2-[2-(Δ2-imidazolinyl)thio]acetanilide is obtained.
MP=170° C.
Rf=0.2 (CHCl$_3$—MeOH : 85-15)

EXAMPLE 5

N-methyl 2'-benzyl-4'-chloro 2-[2-(Δ2-imidazolinyl)thio]acetanilide hydrochloride. (12)

a) 2'-benzyl-4'-chlorotosanilide 8.31 g of tosyl chloride are added to a solution of 2-benzyl-4-chloroaniline (7.9 g) in pyridine (35 ml). After 1 hour at 100° C. followed by cooling, it is poured onto 100 ml of 6N hydrochloric acid and 200 g of ice. A gum forms which is extracted with ethyl acetate. After washing with water, drying and concentrating, 2'-benzyl-4'-chlorotosanilide is obtained by precipitation with petroleum ether (10.85 g).
MP=115° C.

b) N-methyl 2'-benzyl-4'-chlorotosanilide

The above compound (8.82 g) in solution in toluene is treated with benzyltriethylammonium chloride (522 mg), 10N sodium hydroxide solution (23.6 ml), and methyl sulfate (5 ml). After agitation for 30 minutes and being set aside overnight, the mixture is decanted, washed with water and then dried over Na$_2$SO$_4$; N-methyl 2'-benzyl-4'-chlorotosanilide is obtained by crystallization (8.37 g).
MP=114° C.

c) N-methyl 2-benzyl-4-chloroaniline

The preceding product (24.49 g), suspended in acetic acid (50 ml), and 70% sulfuric acid (50 ml), is heated for 11 hours at 100° C. and then poured into 100 ml of ice water. After neutralization with 10N sodium hydroxide, extraction with ether, washing with water and drying, an orange oil (13.16 g) hydrochloride is obtained upon evaporation.
MP=125° C.

d) N-methyl 2'-benzyl-4'-chlorobromoacetanilide

The N-methyl 2-benzyl-4-chloroaniline (10.8 g) in solution in ethyl acetate is treated at 5° C. with 4.9 ml of bromoacetyl bromide. After 1 hour at room temperature, decantation and washing with water, the solution is concentrated. Upon crystallization, N-methyl 2'-benzyl-4'-chloro-bromoacetanilide is obtained (12.21 g).
MP=78° C.

e) N-methyl 2'-benzyl-4'-chloro 2-[2-(Δ2-imidazolinyl)thio]acetanilide hydrochloride The product obtained above (1.76 g) is treated under reflux with ethanol (20 ml) for 2 hours in the presence of ethylene thiourea. After cooling and filtration, 2.19 grams of crude product are obtained. It is taken up in 1N sodium hydroxide, extracted with ethyl acetate, washed with water and then evaporated under vacuum. The residue, when treated with an ethanolic solution of hydrochloric acid, gives, upon crystallization from ethyl ether, N-methyl 2'-benzyl-4'-chloro 2-[2-( Δ2-imidazolinyl)thio]acetanilide (1.7 g).
MP=217° C.
Rf=0.7 (CHCl$_3$—MeOH : 50—50).

EXPERIMENTAL

Various toxicological and pharmacological tests were carried out on the compounds of the present invention.

A - TOXICOLOGY

The compounds of the invention were subjected to examination as to their toxicity. This was determined by the 50% lethal dose (LD$_{50}$). It was determined on lots of ten (10) mice orally and calculated in accordance with the method of Thomson and Weil (Biometrics 1952, 8, 249). The LD$_{50}$ of the compounds tested is greater than 500 mg/kg orally.

B - PHARMACOLOGICAL PROPERTIES

In pharmacological experiments, the compounds of the invention exhibited excellent antiulcer and gastric antisecretory properties. The results obtained with certain products of the present invention are reported below by way of example as compared with cimetidine.

1. Test study of gastric secretion by ligature of the pylorus using Shay's technique (Gastroenterology 5, 53, 1945 and 26, 906, 1954) on male Sprague-Dawley rats. Acute treatment by intraduodenal route in a dose of 50 mg/kg.

| Product | % Variation | |
|---|---|---|
| | decrease of the volume secreted | increase of the intragastric pH |
| Cimetidine | 47 | 90 |
| 1 | 76 | 158 |
| 7 | 70 | 118 |
| 4 | 76 | 267 |
| 16 | 79 | 153 |
| 15 | 50 | 181 |

2. Activity toward ulcers with acetyl salicylic acid quantified in accordance with the Pfeiffer scale (Arch.

Int. Pharmacodyn. 190,'5, 13, 1971) on male rats. Treatment orally, acute.

| Product | Dose (mg/kg) | % Inhibition of the ulcer lesions |
|---|---|---|
| Cimetidine | 40 | 46 |
| 1 | 40 | 34 |
| 7 | 40 | 46 |
| 12 | 40 | 40 |
| 15 | 50 | 35 |
| 16 | 50 | 32 |

C - THERAPEUTIC APPLICATIONS

Based on their pharmacological properties, the compounds of the invention can be used in the treatment of digestive pathology and more particularly of ulcer pathology. The pharmaceutical preparations containing these active principles can be administered orally. It is also possible to combine therewith other pharmaceutically and therapeutically-acceptable active principles.

Those compounds of the present invention comprising a salt-forming group can be administered to man or animal orally or parenterally in the form either of the free base or in the form of a therapeutically-acceptable salt. The new derivatives which are bases can be converted into acid addition salts with acids, which acid addition salts form part of the invention. These acid addition salts can be obtained by reaction of the new basic derivatives with an acid in a suitable solvent, such as for example, in the mineral acid series, hydrochloric, hydrobromic, methanesulphonic, sulphuric, and phosphoric, and in the organic series, acetic, propionic, maleic, fumaric, tartaric, citric, oxalic, and benzoic acid, to name only a few. The selection of the free base or acid addition salt thereof in preparation of the desired acid addition salt in any particular case will be apparent and fully within the capability of one skilled in the art. Such novel compounds of the invention are frequently used in the form of their pharmaceutically-acceptable acid addition salts, such as the hydrochloride, hydrobromide, or the like, since the salt form is usually the best form for pharmaceutical formulations. Innumerable other pharmaceutically-acceptable acid addition salts can be prepared from the hydrochloride or other acid addition salt via the free base in conventional manner.

Based on their pharmacological properties, the compounds of the invention, and more especially the compounds of the Examples, can be used in therapy in the treatment of excessive gastric secretion and ulcers. Pharmaceutical preparations containing these active principles can be administered orally or parenterally. It is also possible to combine them with other pharmaceutically- and therapeutically-acceptable active principles.

On a basis of their pharmacological properties and their relatively low toxicity, the compounds of the invention can be employed for gastric antisecretory effect in a subject in need of the same, as well as for their antiulcer effect in a subject in need of the same, and accordingly may be employed in the form of pharmaceutical preparations which facilitate bioavailability and/or in the form of pharmaceutical compositions thereof containing an effective amount of the active ingredient together with a pharmaceuticallyacceptable carrier, diluent, or adjuvant. The preparations may as usual be provided in solid form, for example, in the form of tablets, pills, capsules, or the like, or in liquid form, for example, in the form of solutions, suspensions, or emulsions. Alternatively, the pharmaceutical preparations may be made available in a form suitable for injection by subjecting the same to conventional pharmaceutical operations such as sterilization, and in any event may contain adjuvants, for instance, preservatives, stabilizers, wetting or emulsifying agents, buffers, and the usual carriers or inert pharmaceutically-acceptable diluents such as sugar, starch, water, or the like. The doses in which the active compounds and the pharmaceutical compositions thereof may be administered vary widely depending upon the subject, but daily doses of from about 0.1 g to 1 mg/kg of body weight and which approximate or are somewhat lower than those usual for Cimetidine may be employed. The pharmaceutical compositions of the invention can be used in human or veterinary medicine where indicated, for instance, in gastric antisecretory and antiulcer therapy and prevention in a subject in need of the same. Other active principles may of course be associated with the compounds of the invention, in order to supplement or reinforce their therapeutic activity within a given pharmaceutical composition or for a given pharmaceutical indication, as is conventional in the art. The exact individual and daily dosages, as well as dosage regimens, will as usual be determined by the physician or veterinarian in charge.

In conclusion, from the foregoing, it is apparent that the present invention provides novel compounds which are useful for their gastric antisecretory and antiulcer properties, a process for the production thereof, pharmaceutical compositions comprising the same, and a method of treating a subject in need of such gastric antisecretory and antiulcer therapy by treating the said subject with an amount of a compound of the invention which is effective for such purpose, all of the foregoing compounds, process, compositions, and method of treating having the foregoing enumerated characteristics and advantages.

It is to be understood that the invention is not to be limited to the exact details of operation or to the exact compounds, compositions, methods, procedures, formulations, or embodiments shown and described, as obvious modifications and equivalents will be apparent to one skilled in the art, and the invention is therefore to be limited only by the full scope which can be legally accorded to the appended claims.

We claim:

1. A thioformamidine selected from those having formula I:

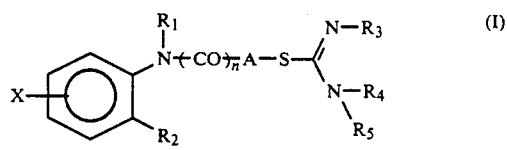

in which:
- $R_1$ represents hydrogen or lower-alkyl containing 1 to 4 carbon atoms, inclusive,
- $R_2$ represents benzoyl, benzyl, or alpha-hydroxybenzyl, the aromatic ring being optionally substituted by a halogen atom,
- $R_3$ and $R_4$ form with the formamidine function a heterocycle selected from imidazole, imidazoline, benzimidazole, triazole, pyrimidine, and tetrahydropyrimidine;

$R_5$ represents hydrogen or lower-alkyl containing 1 to 4 carbon atoms, inclusive, or forms with $R_4$ a double bond ($-N=R_4$) in the case of a pseudoaromatic heterocycle;

n equals 0 or 1;

A represents a linear or branched alkylene group having 1 to 4 carbon atoms, inclusive, X represents hydrogen, halogen, lower $C_{1-4}$ alkyl, lower $C_{1-4}$ alkoxy, or nitro, and pharmaceutically acceptable organic and inorganic salts thereof.

2. A compound according to claim 1, selected from the group consisting of:

N-methyl 2-[2-( Δ2-imidazolinyl)thio]2'-orthochlorobenzoyl-4'-chloroacetanilide hydrochloride;

N-methyl 2-[2-(Δ2-imidazolinyl)thio] 2'-benzoyl-4'-chloroacetanilide hydrochloride;

2-[2-(Δ2-imidazolinyl)thio] 2'-orthochlorobenzoyl-4'-chloroacetanilide hydrochloride;

N-methyl 2-[2-(1-methylimidazolyl)thio] 2'-orthochlorobenzoyl-4'-chloroacetanilide hydrochloride;

2-(2-imidazolylthio) 2'-benzoyl-4'-chloroacetanilide hydrochloride;

2-(2-imidazolylthio) 2'-orthochlorobenzoyl-4'-chloroacetanilide hydrochloride;

N-methyl 2'-orthochlorobenzoyl-4'-chloro 2-[(2-imidazolyl)thio]acetanilide hydrochloride;

1-(2-imidazolylthio) 2-[(2-benzoyl-4-chloro) anilino]ethane;

1-[2-(Δ2-imidazolinyl)thio] 2-(2-benzoyl-4-chloro)anilinoethane;

N-methyl 2'-orthochlorobenzoyl-4'-chloro 2-[2-(1-methyl-Δ2-immidazolinyl)thio] hydrochloride;

N-methyl 2'-(orthochloro- α-hydroxybenzyl)-4'-chloro 2-[2-(Δ2-imidazolinyl)thio]acetanilide;

N-methyl 2'-benzyl-4'-chloro 2-[2-(Δ2-imidazolinyl)thio]acetanilide hydrochloride;

N-methyl 2'-orthochlorobenzoyl-4'-chloro 2-[2-(Δ2-imidazolinyl)thio]propionanilide citrate;

N-methyl 2'-benzoyl 2-[2-imidazolylthio]acetanilide;

N-methyl 2'-benzoyl-4'-chloro 2-(2-imidazolylthio)acetanilide hydrochloride;

N-methyl 2'-orthochlorobenzoyl-4'-chloro 2-(2-pyrimidinyl)thioacetanilide;

N-methyl 2'-orthochlorobenzoyl-4'-chloro 2-(1-ethyl-2-imidazolyl)thioacetanilide hydrochloride;

N-methyl 2'-orthochlorobenzoyl-4'-chloro 3-(2-imidazolyl)thiopropionanilide;

N-methyl 2'-benzoyl-4'-nitro 2-[(2-imidazolyl)thio]acetanilide hydrochloride;

N-methyl 2'-orthofluorobenzoyl-4'-chloro 2-[(2-imidazolylthio]acetanilide hydrochloride; and N-methyl 2'-benzoyl-4'-methoxy 2-[(2-imidazolylthio]acetanilide hydrobromide.

3. A pharmaceutical composition useful as a gastric antisecretory and antiulcer agent, containing as active principle an amount of at least one compound according to claim 1 which is effective for such purpose, together with a pharmaceutically-acceptable carrier or diluent.

4. A pharmaceutical composition useful as a gastric antisecretory and antiulcer agent, containing as active principle an amount of at least one compound according to claim 2 which is effective for such purpose, together with a pharmaceutically-acceptable carrier or diluent.

5. A method of treating a subject in need of gastric antisecretory or antiulcer therapy comprising the step of administering to the said subject an amount of at least one compound of claim 1 which is effective for such purpose.

6. A method of treating a subject in need of gastric antisecretory or antiulcer therapy comprising the step of administering to the said subject an amount of at least one compound of claim 2 which is effective for such purpose.

* * * * *

UNITED STATES PATENT AND TRADEMARK OFFICE
CERTIFICATE OF CORRECTION

PATENT NO. : 5,025,015

DATED : Jun. 18, 1991

INVENTOR(S) : Jean F. Patoiseau, Jean-Marie Autin, Henri Cousse, Véronique Sales, Jacky Tisne-Versailles, Jean-Pierre Bali It is certified that error appears in the above-identified patent and that said Letters Patent is hereby corrected as shown below:

Column 1, line 14; "guanidin e;" should read -- guanidine; --.
Column 4, approximately lines 32/33; move the "e" at the end of line 32 to the beginning of line 33 before "thane".
Column 7, lines 34/35; move the "o]" at the beginning of line 35 to the end of line 34 before the hyphen "-".
Column 7, lines 67/68; move the "o]" at the beginning of line 68 to the end of line 67 before the hyphen "-".
Column 8, line 67; "MeO-" should read -- MeOH- --.
Column 8, line 68; "H-NHCl$_3$-" should read -- -CHCl$_3$- --.
Column 9, lines 32/33; move the "o]" at the beginning of line 33 to the end of line 32 before the hyphen "-".
Column 11, line 65; "pharmaceuticallyacceptable" should read -- pharmaceutically-acceptable --.
Column 13, line 10; move the "ly" at the beginning of line 10 to the end of line 9 before the hyphen "-".
Column 13, line 34; "immidazolinyl" should read -- imidazolinyl --.
Column 14, lines 4/5; move the "o)" at the beginning of line 5 to the end of line 4.
Column 14, lines 12/13; move the "o]" at the beginning of line 13 to the end of line 12.
Column 14, lines 16/17; move the "o]" at the beginning of line 17 to the end of line 16 before the hyphen.

Signed and Sealed this

Twenty-ninth Day of December, 1992

Attest:

DOUGLAS B. COMER

Attesting Officer     Acting Commissioner of Patents and Trademarks